United States Patent [19]

Peters et al.

[11] Patent Number: 5,549,552
[45] Date of Patent: Aug. 27, 1996

[54] BALLOON DILATION CATHETER WITH IMPROVED PUSHABILITY, TRACKABILITY AND CROSSABILITY

[75] Inventors: Jeffrey J. Peters, Golden Valley; Brooke Q. Ren, Brooklyn Park; Christopher R. Larson, St. Paul, all of Minn.

[73] Assignee: SCIMED Life Systems, Inc., Maple Grove, Minn.

[21] Appl. No.: 398,186

[22] Filed: Mar. 2, 1995

[51] Int. Cl.$^6$ ................................................ A61M 29/00
[52] U.S. Cl. ..................... 604/96; 604/264; 604/280; 606/194
[58] Field of Search ................ 604/96–103, 280–282; 606/194, 192

[56] References Cited

U.S. PATENT DOCUMENTS

| | | |
|---|---|---|
| 4,251,305 | 2/1981 | Becker et al. |
| 4,636,272 | 1/1987 | Riggs |
| 4,748,982 | 6/1988 | Horzewski et al. |
| 4,943,278 | 7/1990 | Euteneuer et al. |
| 4,964,409 | 10/1990 | Tremulis |
| 5,047,045 | 9/1991 | Arney et al. |
| 5,050,606 | 9/1991 | Tremulis |
| 5,100,381 | 3/1992 | Burns |
| 5,120,308 | 6/1992 | Hess ............................ 604/96 |
| 5,154,725 | 10/1992 | Leopold |
| 5,156,594 | 10/1992 | Keith |
| 5,159,937 | 11/1992 | Tremulis |
| 5,226,888 | 7/1993 | Arney ........................... 604/96 |
| 5,279,562 | 1/1994 | Sirhan et al. |
| 5,304,134 | 4/1994 | Kraus et al. |
| 5,304,198 | 4/1994 | Samson ......................... 604/96 |
| 5,346,505 | 9/1994 | Leopold |
| 5,370,655 | 12/1994 | Burns |
| 5,387,193 | 2/1995 | Miraki |
| 5,397,306 | 3/1995 | Nobuyoshi et al. |
| 5,480,383 | 1/1996 | Bagaoisan et al. |

FOREIGN PATENT DOCUMENTS

| | | |
|---|---|---|
| 0688576A1 | 6/1995 | European Pat. Off. |
| WO93/17750 | 9/1993 | WIPO |

*Primary Examiner*—Randall L. Green
*Assistant Examiner*—Perry E. Van Over
*Attorney, Agent, or Firm*—Robert E. Atkinson

[57] ABSTRACT

A medical system is disclosed which includes an over-the-wire type balloon catheter and a guide wire wherein the catheter includes a polymer outer tube, and an inner tube having a metallic proximal portion and a polymer distal portion. An inflatable balloon is connected to the distal ends of the inner tube and the outer tube. The guide wire may be removed from and inserted into the guide wire lumen at either end of the catheter. The catheter may further include a transition member traversing the junction between the proximal and distal portions of the inner tube. The transition member may be in the form of a wire, a coil or a tube, and may be made of cold drawn stainless steel or a superelastic alloy. The metallic proximal portion of the inner tube may have a wall thickness greater than or equal to 0.0020 inches and an outside diameter less than or equal to 0.0255 inches. The catheter may also include a radiopaque marker band swaged onto the inner tube.

A method of manufacturing a balloon catheter is also disclosed which includes the steps of: (1) placing a support member inside a tubular member; (2) sliding a balloon over the tubular member such that the bonding region on the tubular member is aligned with a bonding region on the balloon; (3) placing a heat shrinkable tube over the balloon aligned with the bonding regions; (4) exposing the heat shrinkable tube and the bonding regions to heat (e.g. infrared) such that the heat shrinkable tube exerts a compressive force onto the balloon, the bonding regions flow, the balloon bonding region is radially compressed onto the tubular member bonding region, and the bonding regions form a tip which is tapered in a distal direction. A heat shield may be used to expose only the bonding regions and the heat shrinkable tube. An adhesive (e.g. urethane) or a tie polymer may be applied to either of the bonding regions.

15 Claims, 8 Drawing Sheets

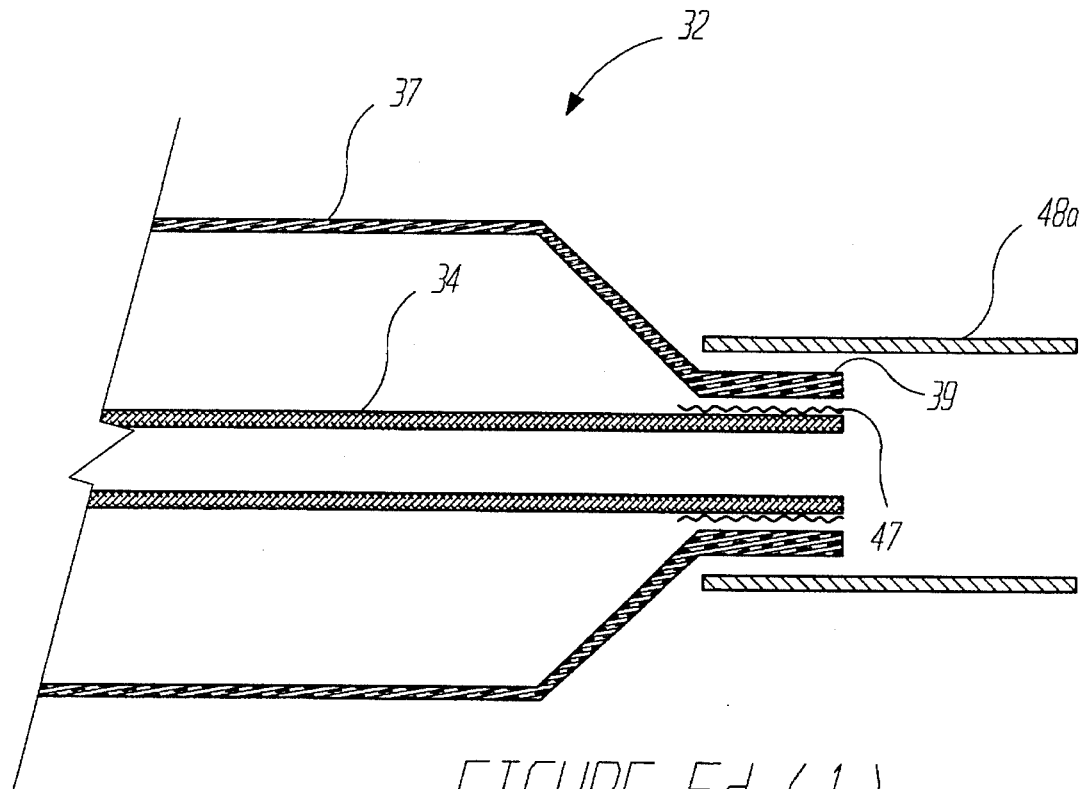
FIGURE 5d (1)
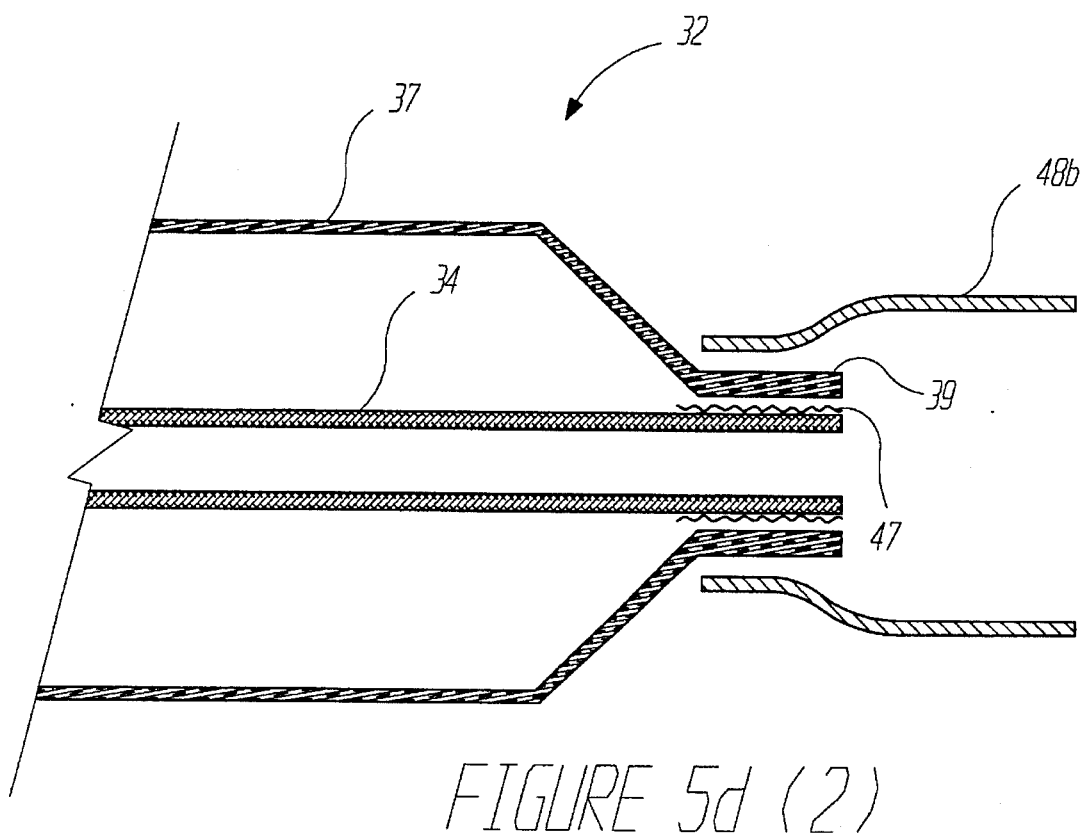
FIGURE 5d (2)

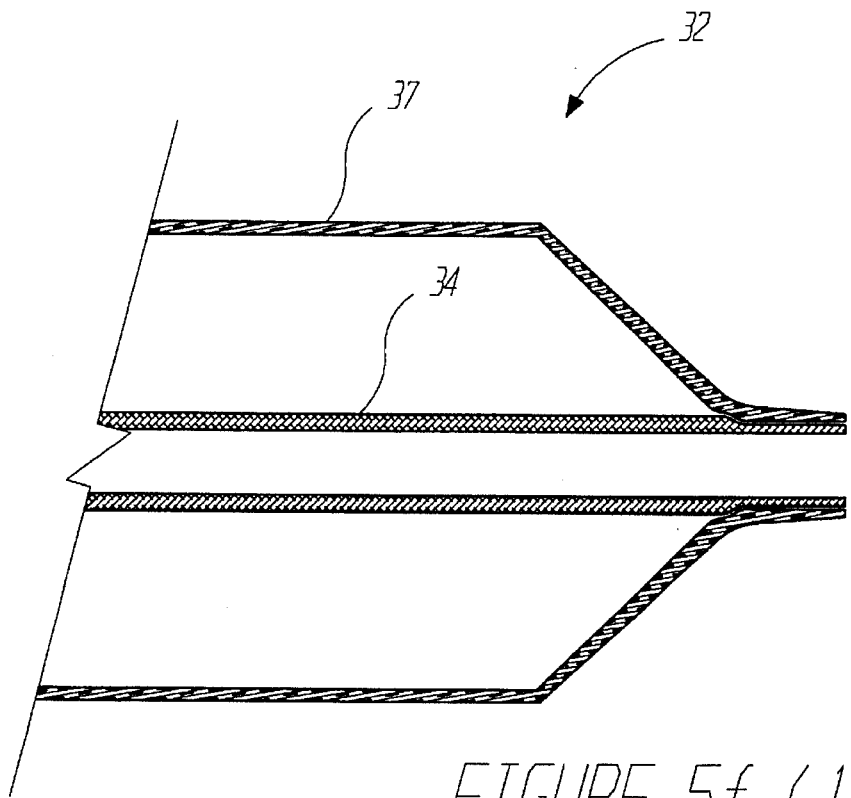
FIGURE 5f (1)
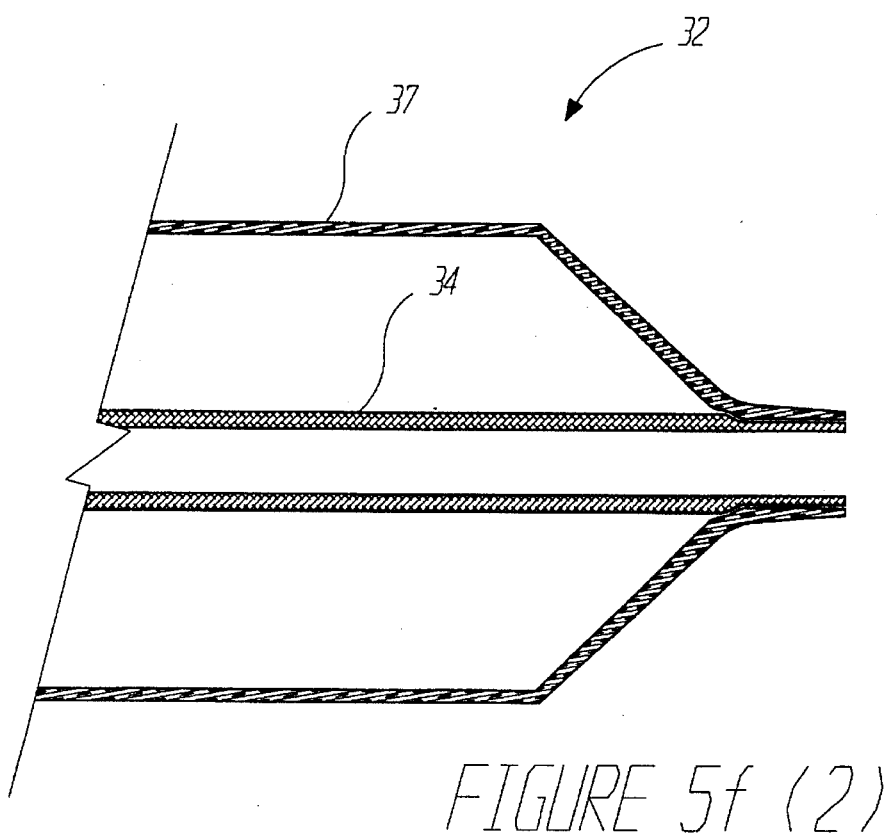
FIGURE 5f (2)

BALLOON DILATION CATHETER WITH IMPROVED PUSHABILITY, TRACKABILITY AND CROSSABILITY

FIELD OF THE INVENTION

The present invention generally relates to medical devices used in combination with guide members. More specifically, the present invention relates to intravascular balloon dilation catheters for use in combination with guide wires. Those skilled in the art will recognize the benefits of applying the present invention to similar fields not discussed herein.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These therapeutic techniques are well-known in the art and typically involve the use of a balloon catheter with a guide wire, possibly in combination with other intravascular devices. A typical balloon catheter has an elongate shaft with a balloon attached to the distal end and a manifold attached to the proximal end. In use, the balloon catheter is advanced over the guide wire such that the balloon is positioned adjacent a restriction in a diseased vessel. The balloon is then inflated and the restriction in the vessel is opened.

There are two basic types of balloon catheters used in combination with a guide wire, namely, over-the-wire (OTW) catheters and single-operator-exchange (SOE) catheters. The construction and use of both OTW catheters and SOE catheters are well-known in the art. An example of an OTW catheter may be found in commonly-assigned U.S. Pat. No. 5,047,045 to Arney et al. An example of an SOE balloon catheter is disclosed in commonly-assigned U.S. Pat. No. 5,156,594 to Keith.

PTA and PTCA catheters are preferably designed to optimize pushability, trackability and crossability. Pushability is defined as the ability to transmit force from the proximal end of the catheter to the distal end of the catheter. Trackability is defined as the ability to navigate tortuous vasculature. Crossability is defined as the ability to navigate the balloon catheter across narrow restrictions in the vasculature.

OTW balloon catheters may be classified into two groups. The first group comprising multi-lumen OTW balloon catheters, and the second group comprising coaxial OTW balloon catheters. Multi-lumen OTW catheters typically include a single extrusion shaft having two side-by-side longitudinally extending lumens, namely an inflation lumen and a guide wire lumen. By contrast, a coaxial OTW catheter typically includes two separate tubes, namely an inner tube and a coaxially disposed outer tube. The inner tube defines a guide wire lumen and an annular inflation lumen is defined between the inner tube and the coaxially disposed outer tube.

Prior art coaxial OTW-type balloon catheters have attempted to maximize pushability by incorporating a stainless steel outer tube on the proximal shaft (also referred to as a hypotube). However, because of the relatively large outside diameter to wall thickness ratio and the relatively low yield strain of stainless steel, such a shaft construction is more prone to kinking than a typical polymer shaft. Currently-marketed coaxial OTW-type balloon catheters typically incorporate a polymer shaft or a reinforced polymer shaft (e.g. composite) as a compromise between maximizing pushability and minimizing the probability of kinking. As such, there is an unmet need for a coaxial OTW-type balloon catheter which satisfies the need for both maximum pushability and minimum propensity to kink.

Prior art OTW and SOE-type balloon catheters have also attempted to improve crossability by minimizing the profile of the deflated balloon. State-of-the-art balloon catheters have a balloon profile which is typically limited by the profile of the distal balloon waist and/or the profile of the balloon at the location of the marker band. Accordingly, it is desirable to have OTW and SOE-type balloon catheters which minimize the profile of the distal balloon waist and minimize the profile of the balloon over the marker band in order to maximize crossability.

SUMMARY OF THE INVENTION

The present invention may be described as a medical system including an over-the-wire type balloon catheter and a guide wire wherein the catheter includes a polymer outer tube, and an inner tube having a metallic proximal portion and a polymer distal portion. The inner tube defines a guide wire lumen and is coaxially disposed inside the outer tube to define an annular inflation lumen therebetween. An inflatable balloon has a distal end connected to the distal end of the inner tube, and a proximal end connected to the distal end of the outer tube. The guide wire has a maximum outside diameter which is less than the minimum inside diameter of the guide wire lumen such that the guide wire may be removed from or inserted into the guide wire lumen at either end of the catheter.

The catheter may further include a transition member traversing the junction between the metallic proximal portion of the inner tube and the polymer distal portion of the inner tube. The transition member may be connected to either the inner tube, the outer tube or both. The transition member may be in the form of a wire, a coil or a tube, and may be made of cold drawn stainless steel or a superelastic alloy.

The metallic proximal portion of the inner tube may have a wall thickness greater than or equal to 0.0020 inches and an outside diameter less than or equal to 0.0255 inches.

The catheter may also include a radiopaque marker band swaged onto the distal polymer portion of the inner tube.

The present invention may also be described a method of manufacturing a balloon catheter which includes the steps of: (1) placing a support member inside a tubular member such that the support member traverses a bonding region on the tubular member; (2) sliding a balloon over the tubular member such that the bonding region on the tubular member is aligned with a bonding region on the balloon; (3) placing a heat shrinkable tube over the balloon such that the heat shrinkable tube is aligned with the bonding region on the balloon and the bonding region on the tubular member; (4) exposing the heat shrinkable tube and the bonding regions to heat from a heat source such that the heat shrinkable tube exerts a compressive force onto the balloon, the balloon bonding region and the tubular member bonding region flow, the balloon bonding region is radially compressed onto the bonding region on the tubular member, and the bonding regions form a tip which is tapered in a distal direction. The heat shrinkable tube may be made of florinated ethylene propylene. The heat source may provide infrared heat.

Prior to exposing the heat shrinkable tube and the bonding regions to heat from the heat source, a heat shield may be placed on the balloon such that only the bonding regions and the heat shrinkable tube are exposed to the heat.

Prior to sliding the balloon member over the tubular member, an adhesive or tie layer polymer may be applied to either the bonding region of the tubular member, the bonding region of the balloon or both. A urethane adhesive may be used and the adhesive may be allowed to partially cure for a period of time.

BRIEF DESCRIPTION OF THE DRAWINGS

FIG. 1A is a side view of a prior art coaxial OTW balloon catheter with a guide wire passing therethrough. FIG. 1B is a side view of a prior art coaxial SOE balloon catheter with a guide wire passing partially therethrough. FIG. 1C is a side cross-sectional view of a distal balloon assembly of a typical prior art coaxial OTW or SOE balloon catheter.

FIGS. 5A–5F(2) are side cross-sectional views illustrating an alternate process for connecting the distal end of the balloon to the inner tube.

DETAILED DESCRIPTION OF THE INVENTION

The following detailed description should be read with reference to the drawings in which like elements in different drawings are numbered identically. The drawings, which are not necessarily to scale, depict selected embodiments and are not intended to limit the scope of the invention.

Examples of constructions, materials, dimensions and manufacturing processes are provided for selected elements. All other elements employ that which is known to those skilled in the field of the invention. Those skilled in the art will recognize that many of the examples provided have suitable alternatives which may also be utilized.

Figure 1A:
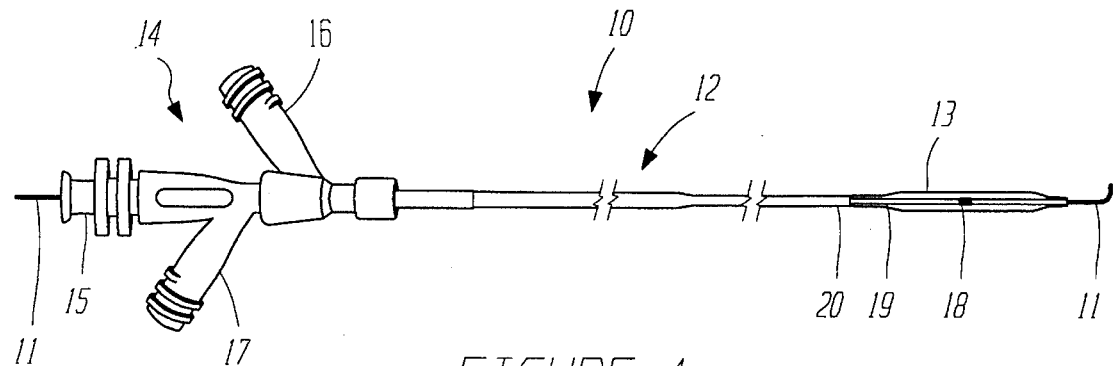
FIGS. 1A–1C are illustrations of the prior art. In particular.
Figure 1B:
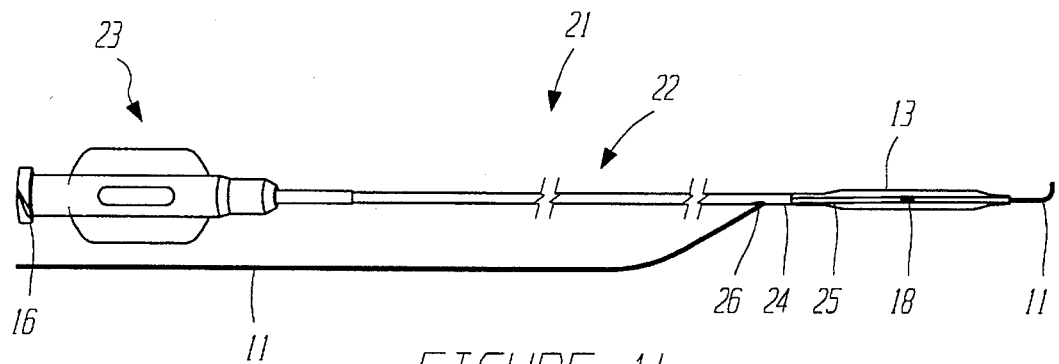
Figure 1C:
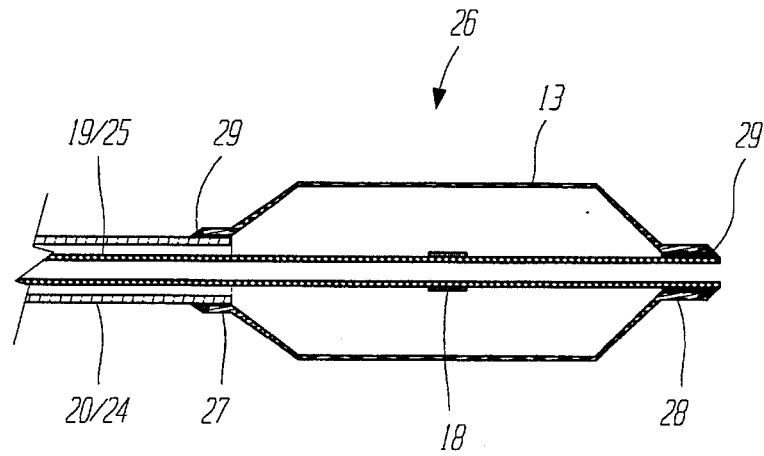

FIGS. 1A–1C are illustrations of prior art balloon catheters which provide a basis for comparison during the discussion of the present invention. FIG. 1A is a side view of a prior art coaxial OTW balloon catheter 10 with a guide wire 11 passing therethrough. A typical coaxial OTW balloon catheter 10 includes an elongate shaft 12 with an inflatable balloon 13 connected to its distal end and a manifold assembly 14 connected at its proximal end. The manifold assembly 14 typically includes a guide wire port 15, an inflation port 16 and a flush port 17. Guide wire port 15 communicates with the inner lumen of the inner tube 19 which in turn provides a passage for the guide wire 11. The inflation port 16 is in fluid communication with the annular lumen between the inner tube 19 and the coaxially disposed outer tube 20 which in turn is in fluid communication with the interior of the balloon 13. Accordingly, balloon 13 may be inflated and deflated by connecting a conventional inflation device (not shown) to inflation port 16. The inflatable balloon 13 is adhesively secured at its proximal end to the distal end of the outer tube 20. The distal end of the inflatable balloon 13 is adhesively secured to the distal end of the inner tube 19. A radiopaque marker band 18 is adhesively secured to the inner tube 19 and provides a means to radioscopically position the balloon within the vasculature of a patient.

FIG. 1B is a side view of a prior art coaxial SOE balloon catheter 21 with a guide wire 11 passing therethrough. A typical SOE balloon catheter 21 includes an elongate shaft 22 with an inflatable balloon 13 connected to its distal end and a manifold 23 connected at its proximal end. The manifold 23 includes an inflation port 16 which is in fluid communication with an inflation lumen passing through the proximal portion of the shaft 22. The distal end of the shaft 22 typically includes an outer tube 24 and an inner tube 25. The inner lumen of the inner tube 25 allows for passage of a guide wire 11. The annular lumen between the inner tube 25 and the coaxially disposed outer tube 24 fluidly connects the interior of the balloon 13 with the inflation lumen passing through the proximal portion of the shaft 22. The proximal end of the inflatable balloon 13 is adhesively connected to the distal end of the outer tube 24. The distal end of the inflatable balloon 13 is adhesively connected to the distal end of the inner tube 25. A radiopaque marker band 18 is adhesively secured to the inner tube 25 and provides a means to radioscopically position the balloon within the vasculature of a patient.

As contrasted against a typical coaxial OTW balloon catheter 10 in which the inner tube 19 extends from the guide wire port 15 to the distal end of the balloon 13, the inner tube 25 on a typical coaxial SOE balloon catheter 21 only extends from a distal guide wire port 26 to the distal end of the balloon 13. Since the inner tube 25 does not extend through the proximal portion of the shaft 22, the outside diameter of the proximal portion of the shaft 22 may be proportionally smaller than the outside diameter of the proximal portion of the shaft 12 on a coaxial OTW catheter 10.

The proximal portion of the shaft 22 on a typical SOE balloon catheter 21 may be made of stainless steel hypotubing and the distal portion of the shaft 22 may be made of a flexible polymer. The stainless steel portion of the shaft 22 may have an outside diameter of approximately 0.024 inches with a corresponding wall thickness of approximately 0.0025 inches. This combination of dimensions and materials provides for a shaft 22 which is substantially pushable and moderately kink resistant at the proximal end and relatively trackable at the distal end.

By contrast, the proximal portion of the shaft 12 on a typical coaxial OTW-type balloon catheter 10 may be made of a polymer or a composite polymer material and the distal end of the shaft 12 may be made of a flexible polymer. The outside diameter of the proximal portion of the shaft 12 typically measures about 0.040 to 0.048 inches with a corresponding wall thickness of approximately 0.004 inches. This combination of dimensions and materials provides for a shaft 12 which is moderately pushable and substantially kink resistant at the proximal end and relatively trackable at the distal end. If the proximal outer portion of the shaft 12 were made of stainless steel, the shaft would be substantially pushable but not very kink resistant.

FIG. 1C is a side cross-sectional view of a distal balloon assembly of a typical coaxial OTW balloon catheter 10 or a typical coaxial SOE balloon catheter 21. The balloon assembly 26 includes an inflatable balloon 13 with a proximal balloon waist 27 adhesively secured to the outer tube 20/24. The inflatable balloon 13 also includes a distal waist 28 adhesively secured to the distal end of the inner tube 19/25. A radiopaque marker band 18 is adhesively secured to the inner tube 19/25 at a mid-point under the inflatable balloon 13. Note that adhesive 29 which is used to connect the proximal balloon waist 27 and the distal balloon waist 28 requires a certain bond gap which inherently adds to the outside diameter at the point of connection. Also note that the marker band 18 adds to the outside diameter of the inner tube 19/25 underneath the balloon 13. Accordingly, when the balloon is folded, the profile of the folded balloon 13 is limited by the outside diameter of the distal balloon waist 28 and the outside diameter of the marker band 18. The profile of the folded balloon 13 determines the ability of the balloon assembly 26 to cross a narrow restriction in a vessel.

Now refer to FIGS. 2 through 5 which illustrate various aspects of the present invention. Exemplary materials and dimensions are given for a PTCA balloon catheter compatible with a guide wire having an outside diameter of about 0.014 inches. Those skilled in the art will recognize that some of the dimensions may be altered in order to have a catheter compatible with a different diameter guide wire.

Figure 2:
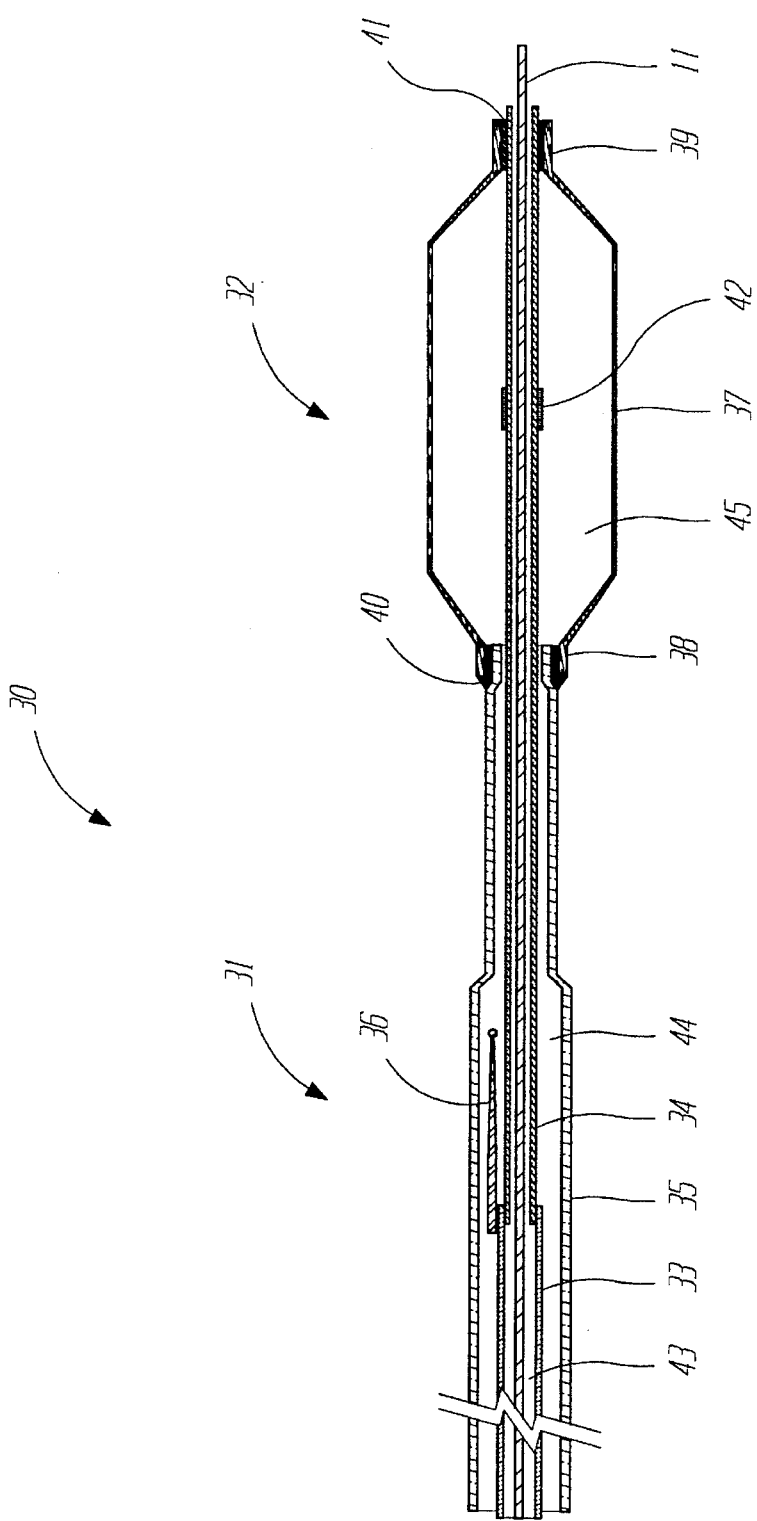
FIG. 2 is a side cross-sectional view of the present invention with a guide wire passing therethrough.

FIG. 2 is a side cross-sectional view of an OTW balloon catheter 30 of the present invention. The balloon catheter 30 includes a shaft assembly 31 with a balloon assembly 32 connected to its distal end. A conventional OTW-type manifold assembly (not shown) is connected to the proximal end of the shaft assembly 31. The shaft assembly 31 includes a proximal inner tube 33 and a distal inner tube 34. An outer tube 35 is coaxially disposed about the proximal inner tube 33 and distal inner tube 34. A stiffness transition member 36 is connected to the distal end of the proximal inner tube 33 and traverses the junction between the proximal inner tube 33 and the distal inner tube 34.

The balloon assembly 32 includes a balloon body portion 37 with a proximal balloon waist 38 and a distal balloon waist 39. The proximal balloon waist 38 is connected to the distal end of the outer tube 35 by means of an adhesive 40. The distal balloon waist 39 is connected to the distal end of the distal inner tube 34 by means of an adhesive 41. An alternate method of connecting the proximal and distal balloon waists 38, 39 is discussed in more detail with reference to FIGS. 5A–5F.

A radiopaque marker band 42 is adhesively secured to the distal inner tube 34 at a mid-point underneath the balloon body 37. An alternate method of connecting the marker band 42 to the distal inner tube 34 is discussed in detail with reference to FIGS. 4A–4C.

The proximal inner tube 33 and the distal inner tube 34 define a guide wire lumen 43 which provides a passage for guide wire 11. Outer tube 35 defines an annular inflation lumen 44 which is in fluid communication with the interior of the balloon 45. The inflation lumen provides a passage for inflation fluid to inflate and deflate the balloon 37.

The proximal inner tube 33 is made of stainless steel, preferably 304v type stainless steel hypotube with a relatively smooth inner surface. The proximal inner may have an outside diameter ranging from 0.0250 to 0.0255 inches and preferably about 0.0253 inches. The proximal inner tube 33 may have an inside diameter ranging from 0.0200 to 0.0210 inches depending on the size of the guide wire 11 that the catheter 30 is designed to be compatible with. The proximal inner tube 33 may have a wall thickness ranging from 0.0020 to 0.00275 inches and preferably about 0.0024 inches. The outside diameter to wall thickness ratio must be sufficiently small to minimize the propensity of kinking. An outside diameter of less than or equal to 0.0255 inches and a wall thickness of greater than or equal to 0.0020 for stainless steel has been shown to significantly reduce the propensity of kinking while significantly increasing the pushability of the proximal portion of the shaft assembly 31.

The distal inner tube 34 is preferably made of HDPE but may also be made of other suitable polymers. The distal inner tube 34 may have an outside diameter ranging from 0.0221 to 0.0231 inches and an inside diameter ranging from 0.0163 to 0.0173 inches depending on the size of the guide wire 11 that the catheter 30 is designed to be compatible with. A distal inner tube 34 made of HDPE with an outside diameter of about 0.0226 inches and an inside diameter of about 0.0168 inches has been found to provide excellent trackability.

Since the stiffness of the metallic proximal inner tube 33 is substantially higher than the stiffness of the polymer distal inner tube 34, a transition member 36 is necessary to prevent kinking of the distal inner tube 34 adjacent the distal end of the proximal inner tube 33. The stiffness transition member 36 may be secured to either the distal end of the proximal inner tube 33, the proximal end of the distal inner tube 34 or both by suitable means such as adhesive, weld, solder, braze, shrink tube, or compression collar. Alternatively, the transition member 36 may be connected to the outer tube 35. The transition member 36 may be in the form of a tapered wire made of stainless steel or superelastic alloy. If a superelastic alloy is employed, pre-plating the wire with nickel provides an improved welding surface. The transition member 36 may have a proximal diameter ranging from 0.0080 to 0.010 inches and tapering to a distal diameter ranging from 0.003 to 0.004 inches. The length of the transition member may range from 3 to 5 inches and is preferably about 4 inches long. The distal end of the transition member 36 is preferably formed to a blunt point to reduce the probability of puncturing the outer tube 35.

The transition member 36 may also be in the form of a partial extension of the proximal inner tube 33. The partial extension may be formed by grinding or cutting away a portion of the proximal inner tube 33 such that a semi-circular tab extends from the distal end. A metal coil (e.g. coiled ribbon) or a polymer tube extending across the junction may also be used as a transition member. The metal coil or polymer tube may be secured to the inner tubes 33, 34 or the outer tube 35. Those skilled in the art will recognize that other suitable alternatives may be employed to reduce the probability that the distal inner tube 34 will kink adjacent the junction to the proximal inner tube 33.

The outer tube 35 may be made of a flexible polymer such as Nylon or HDPE and is preferably made of PEBAX. The proximal portion of the outer tube 35 preferably has an outside diameter ranging from 0.0410 to 0.0420 inches with a wall thickness ranging from 0.0030 to 0.0034. The distal end of the outer tube 35 preferably tapers to an outside diameter ranging from 0.0320 to 0.0331 inches with a corresponding wall thickness ranging from 0.0028 to 0.0032 inches. Those skilled in the art will recognize that other suitable materials, dimensions and tapers may be employed. In addition, a multi-sectional outer tube may be used in place of a single section outer tube 35.

The balloon 37 may be made of conventional materials such as HDPE, PET, POC, nylon or, preferably, polyether block amide (PEBAX) as described in commonly assigned co-pending patent application Ser. No. 397,837, filed on Mar. 2, 1995 entitled "Block Copolymer Elastomer Catheter Balloons" by Wang et al. which is hereby incorporated by reference. The inflatable balloon 37 may have conventional balloon dimensions. Adhesives 40 and 41 may be any suitable medical grade adhesive such as epoxy or urethane. Note that the adhesives 40, 41 used to bond the proximal and distal balloon waists 38, 39 is preferably urethane when the heat bonding technique discussed with reference to FIGS. 5A–5F is employed. Note also that if similar materials are used, adhesives may not be necessary using the heat bonding method described with reference to FIGS. 5A–5F. For example, if PEBAX is used as a material for the outer tube 35 and the balloon assembly 32, adhesive 40 is not necessary to thermally bond the proximal balloon waist 38 to the distal end of the outer tube 35.

Marker band 42 is preferably made of a platinum-iridium alloy but may also be made of other suitable radiopaque materials such as gold. The marker band 42 may have a length ranging from 0.048 to 0.054 inches with an outside diameter ranging from 0.0266 to 0.0283 inches and an inside diameter ranging from 0.0236 to 0.0241 inches. An alternative method of attaching marker band 42 is described in more detail with reference to FIGS. 4A–4C.

With continued reference to FIG. 2, the distal end of the proximal inner tube 33 may be connected to the proximal end of the distal inner tube 34 by several methods. FIG. 2 shows a lap joint with the proximal end of the distal inner tube 34 residing inside the distal end of the proximal inner tube 33. A lap joint length of about 3 to 5 mm provides sufficient bond strength. A suitable medical grade adhesive such as cyanoacrylate or urethane may be used to secure the lap joint.

Figure 3A:
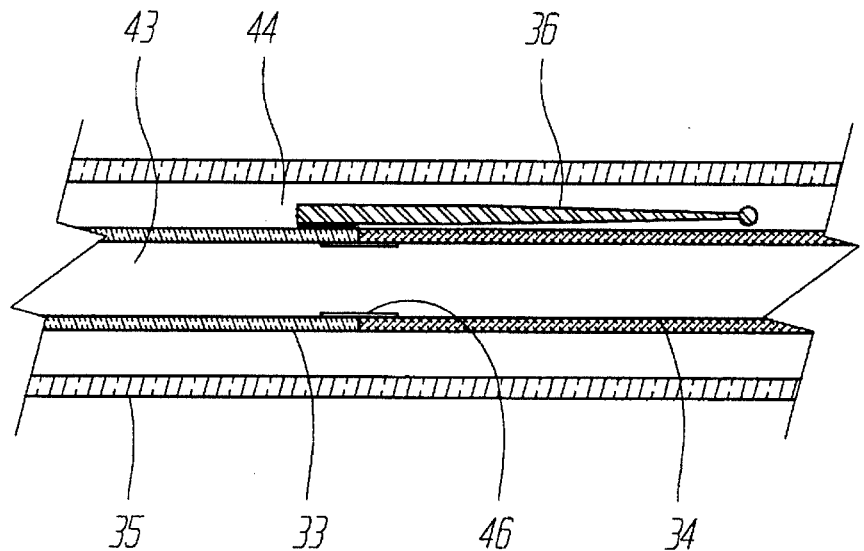
FIGS. 3A and 3B are side cross-sectional views of alternate embodiments of the mid-shaft assembly.
Figure 3B:
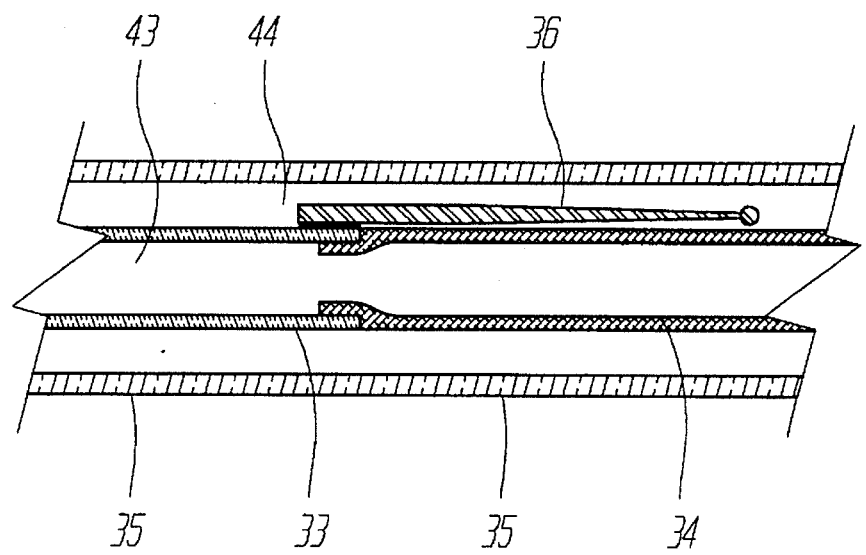

Now refer to FIGS. 3A and 3B which show alternative methods of connecting the proximal inner tube 33 to the distal inner tube 34. In particular, FIG. 3A depicts an alternative embodiment in which the proximal inner tube 33 is connected to the distal inner tube 34 by way of a tubular connector 46. In this embodiment, the inside diameter of the proximal inner tube 33 is substantially the same as the inside diameter of the distal inner tube 34. The tubular connector 46 has an outside diameter sufficient to allow a sliding fit inside inner tubes 33 and 34, a length of about 10 to 15 mm, and a wall thickness of about 0.0010 inches. Alternatively, the tubular connector 46 may be placed on the outside of the proximal and distal inner tubes 33, 34 by increasing the inside diameter of the tubular connector 46 appropriately. The tubular connector 46 may be made of thermoset polyimide, but other suitable materials may be employed. Once again, a suitable medical grade adhesive such as cyanoacrylate or urethane may be used to secure the lap joints.

FIG. 3B depicts a second alternative embodiment in which the proximal end of the distal inner tube 34 is necked-down to fit inside the proximal inner tube 33. The distal inner tube 34 may be necked down by drawing the tube 34 through a heated die. A lap joint length of about 3 to 5 mm provides sufficient bond strength. Once again, a suitable medical grade adhesive such as cyanoacrylate or urethane may be used to secure the lap joint.

Figure 4A:
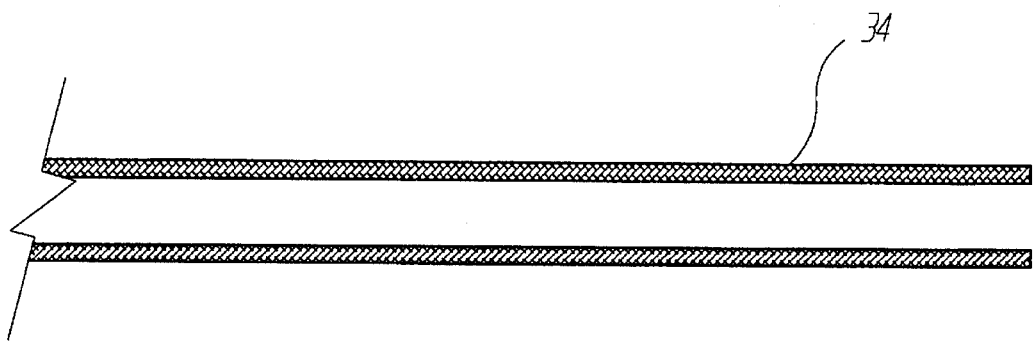
FIGS. 4A–4C are side cross-sectional views illustrating an alternate process for connecting the marker band to a portion of the inner tube passing through the balloon.
Figure 4B:
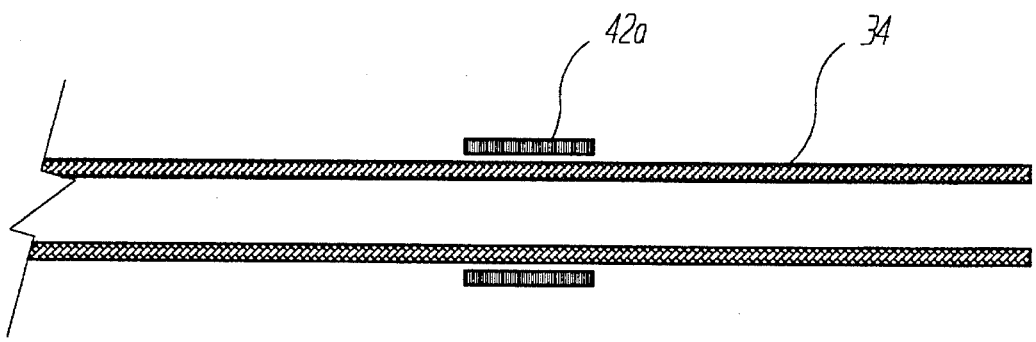
Figure 4C:
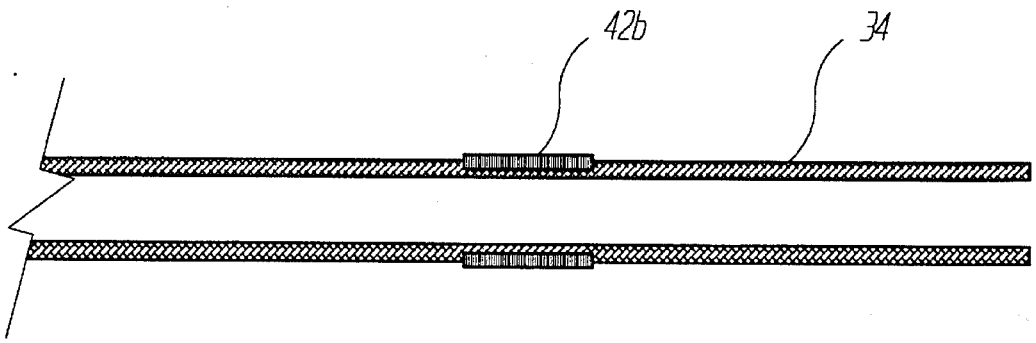

Refer now to FIGS. 4A–4C which are side cross-sectional views illustrating an alternative process for connecting the marker band 42 to a portion of the distal inner tube 34 at a mid-point under the balloon (not shown). A distal inner tube 34 is provided as shown in FIG. 4A and a free-floating marker band 42a is slid over the distal inner tube 34 as shown in FIG. 4B to a position aligned with the longitudinal mid-point of the balloon. The conventional method utilizes an adhesive to secure the free-floating marker band 42a to the inner tube 34. In this alternate process, however, a swaging or cold-forging process is used to uniformly squeeze the marker band 42a onto the distal inner tube 34 until the marker band 42b is substantially the same outside diameter as distal inner tube 34 as shown in FIG. 4C. A suitable radial swaging machine is model no. 111 available from Torrington Swager and Vaill End Forming Machinery, Inc. As compared to the conventional adhesively secured marker band, the swaged marker band 42b does not limit the ability to fold the balloon 37 onto the distal inner tube 34. In addition, the swaged marker band 42b reduces the probability of damaging the inside surface of the balloon 37 which in turn reduces the probability of low pressure balloon failure.

Refer now to FIGS. 5A–5F which are side cross-sectional views illustrating an alternative process for bonding the proximal and distal balloon waists 38, 39. This process is not limited to bonding the balloon waists 38, 39, but may be applied to any joint between two or more polymer tubular members. For purposes of illustration only, the following example considers the joint between the distal balloon waist 39 and the distal polymer tube 34.

Figure 5A:
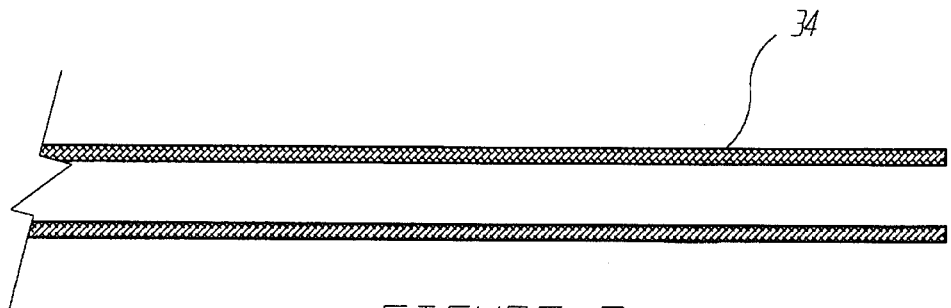
Figure 5B:
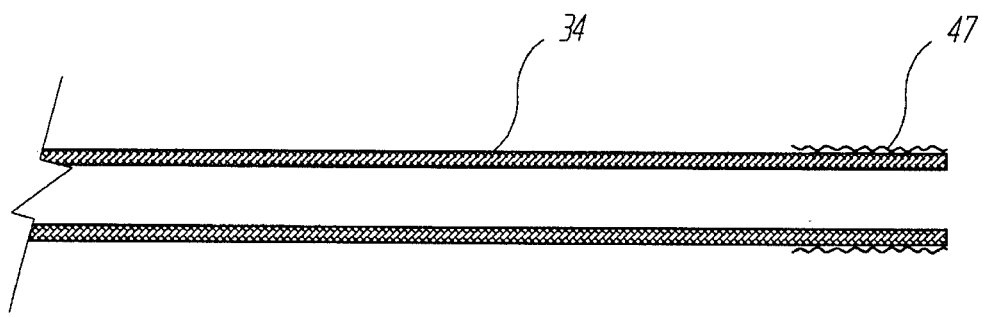
Figure 5C:
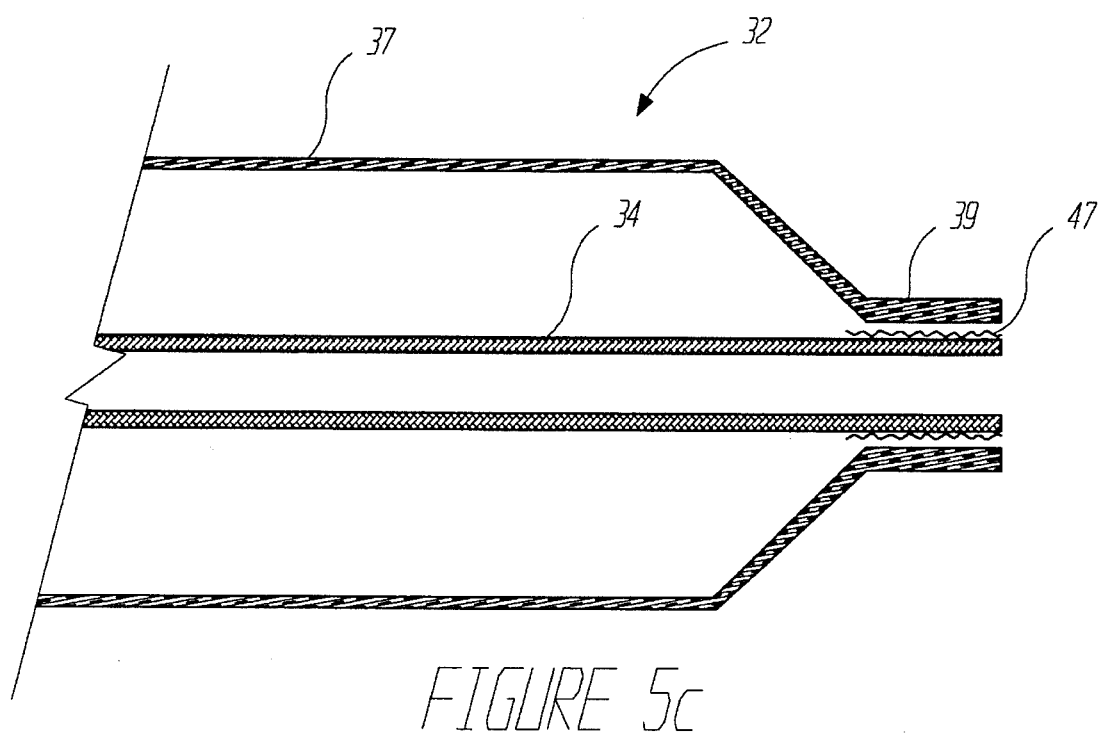
Figure 5E:
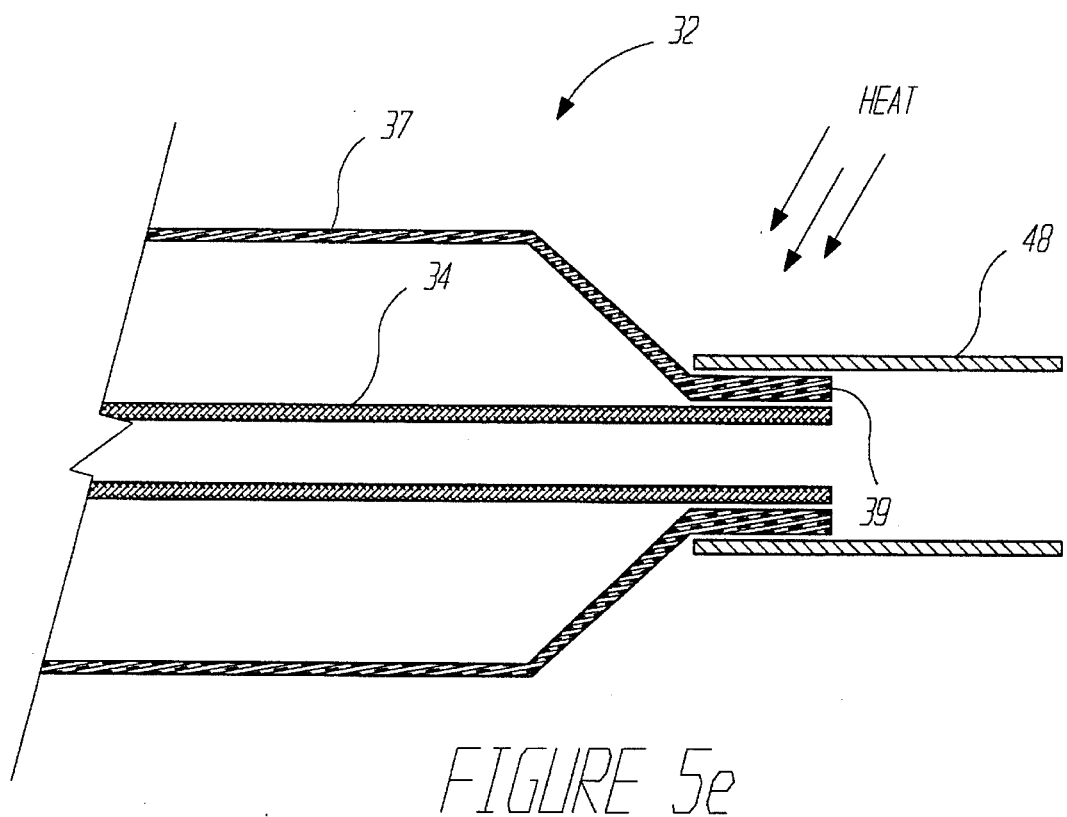

Starting with the distal inner tube 34 as shown in FIG. 5A, an adhesive coating 47 is applied as shown in FIG. 5B. The adhesive coating 47 provides for improved adhesion between dissimilar substrates. If similar substrates are used, it is contemplated that the adhesive 47 would not be necessary. The adhesive coating 47 is applied to the distal 2 inches (the majority of which is trimmed off after the bonding process is complete) of the inner tube 34 by a suitable method such as spray coating. The adhesive coating may alternatively be applied to the distal balloon waist 39 or both the inner tube 34 and the distal balloon waist 39. Depending on the surface characteristics of the bond substrates, it may be desirable to plasma treat the inner tube 34 and/or the balloon bond sites 38, 39 prior to coating either with adhesive. The adhesive coating may be any suitable medical grade adhesive such as epoxy, cyanoacrylate or urethane and is preferably UR 218MF urethane adhesive available from H. B. Fuller. If UR 218MF urethane adhesive is used, the adhesive coating 47 is allowed to cure between 2 to 120 hours. After the initial cure time, the balloon assembly 32 is positioned such that the distal balloon waist 39 is aligned with the adhesive coating 47 as shown in FIG. 5C. A heat shrink tube 48a/48b is then positioned over the distal balloon waist 39 as shown in FIGS. 5D(1) and 5D(2). The heat shrink tube 48a/48b extends distally beyond the distal end of the balloon waist 39 which aids the tapering effect (discussed later). Heat shrink tube 48 may take the form of a uniform tube 48a in FIG. 5D(1) or a tapered tube 48b in FIG. 5D(2). The tapered tube 48b is formed by pre-shrinking one end of the tube 48 using a suitable heat source (e.g. infrared heater preferred, but other heat sources may be adapted). With the heat shrink tube 48a or 48b positioned over the distal balloon waist 39 and an appropriate heat shield positioned proximal therefrom, heat is applied to thermally bond the distal balloon waist 39 to the distal inner tube 34. In applying the heat, the heat shrink tube 48 compresses radially, applying compressive forces to the distal balloon waist 39 and the distal inner tube 34. A support mandrel (previously placed inside the distal inner tube 34 but not shown) provides an equal and opposite radial force. The heat causes the material of the distal balloon waist 39 and the distal inner tube 34 to flow and thin upon compression by the heat shrink tube 48. The heat is then discontinued and the heat shrink tube 48 is removed. The resulting tip formations are shown in FIGS. 5F-1 and 5F-2.

The tip formation shown in FIG. 5F-1 is formed by using a single heat shrink tube 48. During the heating process, the distal balloon waist 39 and the distal end of the distal inner tube 34 tend to flow and thin out in the distal direction. As such, the tip formation is tapered in a distal direction. The tapering feature is advantageous because it improves the ability of the catheter 30 to cross tight restrictions in the vasculature.

The tip formation shown in FIG. 5F-2 is formed by using a first heat shrink tube with a first recovered diameter and subsequently applying a second heat shrink tube with a second recovered diameter, wherein the second recovered diameter is less than the first recovered diameter. The second heat shrink tube is placed slightly distal from the position of the first heat shrink tube such that the resulting tip formation has a proximal diameter greater than the distal diameter.

The heat shrinkable tube 48 may be made of florinated ethylene propylene (FEP, also known as poly florinated ethylene propylene, PFEP) and is preferably transparent with a non-stick surface. The transparency allows infrared radiation to partially pass through the heat shrink tube 48 and be absorbed by the balloon waist 39 and the inner tube 34. The non-stick surface allows the heat shrink tube 48 to be easily removed from the bond site after the heating process is complete.

It is contemplated that a tie layer polymer such as modified HDPE may be used in place of the adhesive 47. Such a tie layer may be co-extruded over the inner tube 34 or applied by a spray coating. If the spray coating method is employed, the tie polymer may be dissolved in a solvent such as xylene and applied with a heated sprayer.

For PTCA balloons, a FEP heat shrink tube 48a with a recovered inside diameter of about 0.018 produces tip formations as depicted in FIG. 5F(1) with a proximal diameter of about 0.025–0.029 inches (depending on the balloon size) tapering to about 0.018 inches distally. A first FEP heat shrink tube 48a with a recovered inside diameter of about 0.025 inches and a subsequent heat shrink tube 48a with a recovered inside diameter of about 0.018 inches produces tip formations as depicted in FIG. 5F(2) with a proximal diameter of about 0.025–0.029 inches (depending on the balloon size) extending for about 1–2 mm and then tapering to about 0.018 inches distally. The two step method is better suited for larger balloon sizes due to the relatively greater amount of polymer material at the bond site. It is anticipated that the tip formation shown in FIG. 5F(1) will provide excellent tip flexibility and that the tip formation shown in FIG. 5F(2) will provide excellent bond strength. Both formations provide for substantially improved crossability.

The tapered heat shrink tube 48b as depicted in FIG. 5D(2) allows the proximal end of the tube 48b to shrink before the distal end of the tube. This causes the radial forces applied to the balloon waist 39 to propagate distally as the heat is applied. This reduces the potential for non-uniform recovery of the heat shrink tube 48b.

The support member discussed above but not shown in the figures may be a stainless steel mandrel with a diameter roughly corresponding to the inside diameter of the distal inner tube 34. The mandrel may be colored a dark color in order to absorb more infrared heat. In a similar manner, the distal polymer inner tube 34 may be colored (e.g. black iron oxide colorant added to polymer) to absorb more infrared heat. The mandrel may also be coated with a lubricious material such as PTFE so avoid adhesion to the inner surface of the inner tube 39.

The catheter of the present invention may be used in the same conventional manner as a typical coaxial OTW balloon catheter while making appropriate adjustments for the improved pushability, trackability and crossability.

While the specification describes the preferred constructions, materials and dimensions, methods of manufacture and methods of practice, those skilled in the art will appreciate the scope and spirit of the invention with reference to the appended claims.

We claim:

1. A medical system, comprising:
   a. an over-the-wire type balloon catheter, the catheter comprising:
      i. a polymer outer tube having a proximal end and a distal end;
      ii. an elongate inner tube having a metallic proximal portion, a polymer distal portion and a guide wire lumen extending therethrough, the guide wire lumen having a minimum inside diameter, the inner tube being coaxially disposed within the outer tube to define an annular inflation lumen therebetween, wherein the distal portion of the metallic inner tube and the proximal portion of the polymer inner tube are connected at a junction;
      iii. a flexible transition member traversing the junction, the flexible transition member having a proximal end and a distal end, wherein one end is free and the other end is fixed; and
      iv. an inflatable balloon having a proximal end, a distal end and an interior, the proximal end of the balloon connected to a distal end of the distal portion of the inner tube, the proximal end of the balloon connected to the distal end of the outer tube, the interior of the balloon being in fluid communication with the inflation lumen; and
   b. a guide wire removably disposed in the guide wire lumen, the guide wire having a maximum outside diameter which is less than the minimum inside diameter of the guide wire lumen.

2. A medical system as in claim 1 wherein the transition member is a wire.

3. A medical system as in claim 2 wherein the transition member is connected to the metallic proximal portion of the inner tube.

4. A medical system as in claim 3 wherein the transition member is made of cold drawn stainless steel.

5. A medical system as in claim 3 wherein the transition member is made of a superelastic alloy.

6. A medical system as in claim 1 wherein the transition member is a coil.

7. A medical system as in claim 1 wherein the transition member is a tube.

8. A medical system as in claim 1 wherein the metallic proximal portion of the inner tube has a wall thickness greater than or equal to 0.0020 inches.

9. A medical system as in claim 8 wherein the metallic proximal portion of the inner tube has a outside diameter less than or equal to 0.0255 inches.

10. A medical device as in claim 1 wherein the catheter further includes a radiopaque marker band swaged onto the distal polymer portion of the inner tube.

11. A medical system as in claim 1 wherein the transition member is a semi-circular extension of the metallic proximal portion.

12. A medical system as in claim 1 wherein the proximal end of the transition member is fixed and the distal end is free.

13. A medical system as in claim 1 wherein the proximal end of the transition members free and the distal end is fixed.

14. A medical system as in claim 1 wherein the fixed end of the transition member is affixed to the polymer outer tube.

15. A medical system as in claim 1 wherein the fixed end of the transition member is affixed to the elongate inner tube.

\* \* \* \* \*